United States Patent [19]

Nakamura et al.

[11] 4,059,613
[45] Nov. 22, 1977

[54] FLUORINE-CONTAINING DICARBAMATE ESTERS

[75] Inventors: Yasusi Nakamura; Masashi Umemura; Michimasa Yonekura, all of Tokyo, Japan

[73] Assignee: Asahi Denka Kogyo K.K., Tokyo, Japan

[21] Appl. No.: 646,921

[22] Filed: Jan. 6, 1976

Related U.S. Application Data

[62] Division of Ser. No. 511,272, Oct. 2, 1974, Pat. No. 3,952,075.

[30] Foreign Application Priority Data

| Oct. 3, 1973 | Japan | 48-111225 |
|---|---|---|
| Oct. 3, 1973 | Japan | 48-111226 |
| Oct. 3, 1973 | Japan | 48-111227 |
| Oct. 3, 1973 | Japan | 48-111229 |
| Nov. 24, 1973 | Japan | 48-132040 |
| Nov. 24, 1973 | Japan | 48-132041 |
| Nov. 24, 1973 | Japan | 48-132042 |
| Nov. 24, 1973 | Japan | 48-132043 |
| Nov. 24, 1973 | Japan | 48-132044 |
| Nov. 24, 1973 | Japan | 48-132045 |
| Dec. 28, 1973 | Japan | 49-113 |
| Dec. 28, 1973 | Japan | 49-114 |
| Dec. 28, 1973 | Japan | 49-115 |
| Dec. 28, 1973 | Japan | 49-116 |
| Dec. 28, 1973 | Japan | 49-118 |
| Dec. 28, 1973 | Japan | 49-119 |
| Aug. 10, 1974 | Japan | 49-65763 |
| Aug. 10, 1974 | Japan | 49-65764 |
| Aug. 10, 1974 | Japan | 49-65768 |
| Aug. 10, 1974 | Japan | 49-65769 |
| Aug. 10, 1974 | Japan | 49-65770 |
| Aug. 10, 1974 | Japan | 49-65771 |

[51] Int. Cl.$^2$ .......................................... C07C 125/06
[52] U.S. Cl. ............................................ 560/26; 252/3; 252/51.5 R; 252/95; 560/158
[58] Field of Search ............ 260/471 C, 482 B, 468 E

[56] References Cited

U.S. PATENT DOCUMENTS

| 3,721,700 | 3/1973 | Schuiever et al. | 260/471 C |
|---|---|---|---|
| 3,899,484 | 8/1975 | Walter | 260/239 EP |
| 3,925,438 | 12/1975 | Brecht et al. | 260/456 A |

*Primary Examiner*—Donald G. Daus
*Assistant Examiner*—Lisa Jones
*Attorney, Agent, or Firm*—Blanchard, Flynn, Thiel, Boutell & Tanis

[57] ABSTRACT

The fluorine-containing organic compound has the general formula:

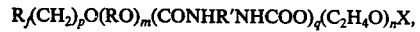

$$R_f(CH_2)_pO(RO)_m(CONHR'NHCOO)_q(C_2H_4O)_nX,$$

wherein $R_f$ is a perfluoro alkyl group; R is an alkylene group; R' is a hydrocarbylene group; X is H, —PO$_3$H$_2$ or —SO$_3$H; m and n are one of 0 and 1 to 50; p is one of 1 to 10; and q is 0 or 1, and is suited for a surface active agent having a high level of the surface activating property at a practical concentration.

10 Claims, No Drawings

FLUORINE-CONTAINING DICARBAMATE ESTERS

This is a division of application Ser. No. 511,272, filed Oct. 2, 1974, now U.S. Pat. No. 3,952,075.

BACKGROUND OF THE INVENTION

1. Field of the Invention

This invention relates to novel fluorine-containing compounds. More particularly, this invention relates to novel fluorine-containing surface active agents. Further, this invention relates to a fluorine-containing surface active agent suitable for emulsifying or finely dispersing fluorine-containing organic compounds. Still further, this invention relates to a fluorine-containing surface active agent particularly suitable for emulsifying or finely dispersing a fluorine-containing organic compound in the gas, liquid or solid phase. Still in addition, this invention relates to a fluorine-containing surface active agent which is valuable as an effective ingredient of a fire extinguishing composition of the aqueous film type.

2. Description of the Prior Art

A great number of fluorine-containing surface active agents are known in the prior art, but only a very limited number of them are industrially valuable. It is known that some of these valuable fluorine-containing surface active agents have a relatively highly activating property at practical concentrations as compared with other surface active agents, but the application field of such fluorine-containing surface active agents is very limited and special techniques are required to attain the intended effects. Further, because of the hydrophobic and oleophilic characteristics of the fluorinated hydrocarbon moiety, special limitations are imposed on compounding of these fluorine-containing surface active agents. For example U.S. Pat. No. 2,723,999 discloses the adducts from fluorine-containing alcohols and ethylene oxide, propylene oxide or the mixture of ethylene oxide and propylene oxide (random polyether), but these adducts do not have sufficient surface activities. U.S. Pat. No. 3,721,700 discloses the adducts from fluorine-containing alchols, tolylene diisocyanate and polyethylene glycol, but these adducts also do not have sufficient surface activities.

By virtue of their peculiar properties and functions, fluorine-containing organic compounds (fluorine-containing carbon compounds) have prominent effects in some special uses, but handling and processing of these compounds are generally difficult and development of surface active agents capable of effectively emulsifying or finely dispersing these fluorine-containing organic compounds has been desired in the art. However, since these fluorine-containing compounds have both hydrophobic and oleophilic characteristics, it is very difficult to find a suitable emulsifier applicable to these compounds. For example, in preparing fluorine-containing resins by emulsion polymerization, more specifically, in homopolymerizing polymerizable fluorine-containing monomers or copolymerizing them with other polymerizable monomers according to the emulsion polymerization method, perfluorocarboxylic acid ($C_9$) or its salt has heretofore been used as a practical emulsifier. Use of salts of sulfuric acid esters of fluorine-containing alcohols and salts of phosphoric acid esters of fluorine-containing alchols has been tried but it has been found that no satisfactory results can be obtained by these compounds. Further, even in the former type emulsifier, improvements of activities and properties have been desired in the prior art. Further, in case an oxygen-transfusive agent for preservation of organs or blood transfusion of hemorrhage patients is prepared by emulsifying an oxygen-dissolving polyfluorinated organic compound, a non-ionic surface active agent of the polyoxypropylene-polyoxyethylene block polyether type has heretofore been used optionally in combination with lecithin, but the emulsion stability of the resulting oxygen-transfusive agent is insufficient and this results in the toxicity of the oxygen-transfusive agent, and the destruction of the emulsion or fine dispersion caused at the high-temperature sterilization step, which is an indispensable treatment, is a fatal defect of the oxygen-transfusive agent of this type. This technical problem is not at all solved by use of known fluorine-containing surface active agents such as non-ionic surface active agents of the N-hydroxyethylperfluoroalkyl sulfonamide type and perfluorocarboxylates. Still further, in preparing surface-treating fine dispersions for formation of surface-protective coatings or lubrication by finely dispersing fluorine-containing resins, fluorinated graphite and the like, dispersing is accomplished only by mechanical operations and development of surface active agents effective for accomplishing the dispersing treatment has been desired also in this field.

SUMMARY OF THE INVENTION

It is therefore a primary object of this invention to provide a novel fluorine-containing organic compound having a surface activating property. More particularly, the primary object of this invention is to provide a fluorine-containing surface active agent having a high level of the surface activating property at a practical concentration condition and which is broadly applicable to various uses with a good compounding property. Another object of this invention is to provide a novel process according to which fluorine-containing organic compounds can be effectively emulsified and dispersed. More specifically, according to this invention, there is provided a fluorine-containing surface active agent which is especially suitable as an emulsifier to be used for formation of fluorine-containing resins by emulsion polymerization and as an emulsifier to be used for preparation of an oxygen-transfusive agent composed mainly of polyfluorinated organic compounds and which can give emulsions and oxygen-transfusing agents of high quality which are stable even after high-temperature sterilization, and which is also used effectively for preparing finely dispersed surface treating agents of the fluorine-containing or fluorinated graphite type.

The compounds of this invention are the compounds having the general formula:

$$R_f(CH_2)_pO(RO)_m(CONHR'NHCOO)_q(C_2H_4O)_nX \qquad (I)$$

wherein $R_f$ is a perfluoroalkyl group having from 4 to 14 carbon atoms; R is an alkylene group having from 2 to 4 carbon atoms and when $q$ is 0 and X is a hydrogen atom, R is an alkylene group having from 3 to 4 carbon atoms; R' is a hydrocarbylene group having from 2 to 8 carbon atoms; X is a member selected from the group consisting of a hydrogen atom, $-PO_3H_2$, its salts, $-SO_3H$ and its salts and when $q$ is 1, X is a hydrogen atom; $m$ is a number selected from the group consisting of 0 and from 1 to 50, preferably 0 or from 1 to 25 and when $q$ is 1 or when X is a hydrogen atom, $m$ is a number of from 1 to 50; $n$ is a number selected from the group consisting of 0 and from 1 to 50, preferably 0 or from 1 to 25, and when X is a hydrogen atom or when $m$ is 0, $n$ is a number of from 1 to 50; $p$ is a number of from 1 to 10, preferably, from 1 to 2 and the fluorine-containing alkyl group having the general formula $R_f(CH_2)_p$— has from 6 to 16 carbon atoms; and $q$ is a number selected from the group consisting 0 and 1 and when $m$ is 0, $q$ is 0.

The fluorine-containing alcohol corresponding to the fluorine-containing oxyalkyl group having the general formula $R_f(CH_2)_pO$— in general formula (I) and (I-1), (I-2) and (I-3), as defined hereunder, includes straight or branched fluorine-containing alchols having from 8 to 14 carbon atoms such as 1,1,2,2-tetrahydro-perfluoroalkanol, 1,1,2,2,3,3-hexahydro-perfluoroalkanol, 1,1,2,2,3,3,4,4-octahydro-perfluoroalkanol, 1,1,2,2,3,3,4,4,5,5-decahydroperfluoroalkanol and 1,1,2,2,3,3,4,4,5,5,6,6-dodecahydroperfluoroalkanol.

In the general formula (I) and (I-3), the group R' includes alkylene group, arylene group and alkarylene group. The organic diisocyanates (R'(NCO)$_2$) corresponding to the general formula —CONHR'NHCO— include aromatic and aliphatic diisocyanates having from 4 to 10 carbon atoms such as hexamethylenediisocyanate, 2,4-tolylenediisocyanate, 2,6-tolylenediisocyanate, 1,4-naphtylenediisocyanate, 1,5-naphtylenediisocyanate, 1,3-phenylenediisocyanate, 1,4-phenylenediisocyanate, isopropylbenzene-2,4-diisocyanate and ω,ω'-diisocyanate-1,2-dimethylbenzene.

The salts of phosphoric ester or sulfuric ester indicated in the general formula (I) and (I-2) include alkali metal salts (such as lithium salt, sodium salt potassium salt), ammonium salt, amine salts (such as ethanolmine salt, triethanolamine salt, propanolamine salt and tripropanolmine salt).

The preferable compounds included in the above general formula (I) are the compounds having the following general formula (I-1), (I-2) and (I-3):

$$R_f(CH_2)_pO(C_3H_6O)m_1(C_2H_4O)n_1H \quad (I-1)$$

wherein $R_f$ is a perfluoroalkyl group having from 4 to 14 carbon atoms; $m_1$ is a number of from 1 to 50, preferably, from 1 to 15, more preferably, from 5 to 15; $n_1$ is a number of from 1 to 50, preferably 1 to 25; $p$ is a number of from 1 to 10, preferably 1 or 2 and the fluorine-containing alkyl group having the general formula $R_f(CH_2)_p$-(has from) 6 to 16 carbon atoms.

$$R_f(CH_2)_pO(C_3H_6O)_m(C_2H_4O)_nX' \quad (I-2)$$

wherein $R_f$ is a perfluoroalkyl group having from 4 to 14 carbon atoms; $m$ is a number of 0 or from 1 to 50, preferably 0 or from 1 to 25, more preferably, 0 or from 1 to 15; $n$ is a number of 0 or from 1 to 50, preferably 0 or from 1 to 25, more preferably 0 or from 1 to 15 but when $m$ is 0, $n$ is not 0, $p$ is a number of from 1 to 10, preferably 1 or 2 and the fluorine-containing alkyl group having the general formula $R_f(CH_2)_p$— has from 6 to 16 carbon atoms; X' is a member selected from the group consisting of —PO$_3$H$_2$—, —SO$_3$H and their salts.

$$R_f(CH_2)_pO(RO)m_1CONHR'NHCOO(C_2H_4O)n_1H \quad (I-3)$$

wherein $R_f$ is a perfluoroalkyl group having from 4 to 14 carbon atoms; R is ethylene or propylene group; $m_1$ is a number of from 1 to 50, preferably, from 1 to 15; $n_1$ is a number of from 1 to 50, preferably, from 10 to 25; $p$ is a number of from 1 to 10, preferably, 1 or 2 and the fluorine-containing alkyl group having the general formula $R_f(CH_2)_p$— has from 6 to 16 carbon atoms.

Preferable examples having the general formula (I-1) are as follows:

| | |
|---|---|
| $C_7F_{15}CH_2O(C_3H_6O)_{10}(C_2H_4O)_3H$ | (I-1-a) |
| $C_6F_{13}CH_2CH_2O(C_3H_6O)_{10}(C_2H_4O)_5H$ | (I-1-b) |
| $C_6F_{13}CH_2CH_2O(C_3H_6O)_{10}(C_2H_4O)_{10}H$ | (I-1-c) |
| $C_{10}F_{21}CH_2CH_2O(C_3H_6O)_5(C_2H_4O)_5H$ | (I-1-d) |
| $C_{10}F_{21}CH_2CH_2O(C_3H_6O)_5(C_2H_4O)_{10}H$ | (I-1-e) |
| $C_{10}F_{21}CH_2CH_2O(C_3H_6O)_{10}(C_2H_4O)_{15}H$ | (I-1-f) | and compounds produced and/or used in below-described Examples.

Preferable examples having the general formula (I-2) are as follows:

| | |
|---|---|
| $C_7F_{15}CH_2O(C_2H_4O)SO_3Na$ | (I-2-a) |
| $C_7F_{15}CH_2O(C_2H_4O)_5SO_3Na$ | (I-2-b) |
| $C_7F_{15}CH_2O(C_2H_4O)_5PO_3Na_2$ | (I-2-c) |
| $C_6F_{13}CH_2CH_2O(C_2H_4O)_5PO_3Na_2$ | (I-2-d) |
| $C_6F_{13}CH_2CH_2O(C_3H_6O)_{10}(C_2H_4O)_5SO_3Na$ | (I-2-e) |
| $C_6F_{13}CH_2CH_2O(C_3H_6O)_{10}(C_2H_4O)_5PO_3Na_2$ | (I-2-f) |
| $C_{10}F_{21}CH_2CH_2O(C_3H_6O)_5(C_2H_4O)_5SO_3Na$ | (I-2-g) |
| $C_{10}F_{21}CH_2CH_2O(C_3H_6O)_5(C_2H_4O)_5PO_3Na_2$ | (I-2-h) |
| $C_{10}F_{21}CH_2CH_2O(C_3H_6O)_{10}(C_2H_4O)_5PO_3Na_2$ | (I-2-i) | and compounds produced and/or used in the below-described Examples.

Preferable examples having the general formula (I-3) are as follows:

| | |
|---|---|
| $C_7F_{15}CH_2O(C_2H_4O)_5CONHC_6H_3(CH_3)NH$-$COOC_2H_4OH$ | (I-3-a) |
| $C_6F_{13}CH_2CH_2O(C_2H_4O)_5CONHC_6H_3(CH_3)NH$-$COO(C_2H_4O)_{10}H$ | (I-3-b) |
| $C_6F_{13}CH_2CH_2O(C_3H_6O)_5CONHC_6H_3)NH$-$COO(C_2H_4O)_{15}H$ | (I-3-c) |
| $C_{10}F_{21}CH_2CH_2O(C_3H_6O)_5CONHC_6H_3)NH$-$COO(C_2H_4O)_{15}H$ | (I-3-d) |
| $C_{10}F_{21}CH_2CH_2O(C_2H_4O)_5CONHC_6P_3(CH_3)NH$-$COO(C_2H_4O)_{10}H$ | (I-3-e) | and compounds produced and/or used in the below-described Examples.

The compound having the general formula (I) can be obtained, for example, by the reaction of the fluorine-containing alcohol having the general formula $R_f(CH_2)_pOH$ corresponding to the $R_f(CH_2)_pO$ group in the general formula (I) with one or more alkylene oxides corresponding to the RO group and $C_2H_4O$ group in the general formula (I) at one stage or multi-stage, and then, if necessary, by the phosphoric- or sulfuric-esterification of the product or by the reaction of the product, polyoxyethylene glycol and organic diisocyanate.

For example, the compound having the general formula (I-1) is obtained by the reaction of fluorine-containing alcohol ($R_f(CH_2)_pOH$) with propylene oxide at the first stage, and then with ethylene oxide. And, for example, the compound having the general formula (I-2) is obtained by the phosphoric- or sulfuric-esterification of the block or non-block adduct obtained from fluorine-containing alcohol and propylene oxide and/or ethylene oxide, and then, if the salt is desired, the product is neutralized. And, for example, the compound having the general formula (I-3) is obtained by the reaction of polyoxyethylene glycol corresponding to the group $(C_2H_4O)_nH$ in the formula, organic diisocyanate corresponding to the group CONHR'NHCO in the formula and the block or non-block adduct obtained from fluorine-containing alcohol and ethylene oxide and/or the alkylene oxide corresponding to the group $(RO)_m$ in the formula.

The reaction between the fluorine-containing alcohol and the alkylene oxide proceeds in the presence of the catalysts known as the catalysts for the alcohol-alkylene oxide reaction, such as basic catalysts (for example, sodium hydroxide, potassium hydroxide, tertiary amines and their aqueous solution etc.) and acidic catalysts (for example, boron trifluoride and boron trifluoride-diethyletherate etc.) and under a pressure of from atmosphere to compressed pressure, at one stage or multi-stage. For example, the adduct is obtained by the reaction of a stoichiometric ratio of fluorine-containing alcohol and alkylene oxide in the presence of the sodium hydroxide-water catalyst system, in accordance with the description of Technical News of of the Government Industrial Research Institute, Nagoya No. 261 (February 1973) and the Extended abstract of 15th. Presentation Meeting of the Government Industrial Research Institute, Nagoya, Technical Materials 48–2, page 224–226, R. Tatematsu et al. (published by the Industrial Technical Association of Nagoya).

Uses of compounds of this invention will now be described.

For example, when the compound of this invention is used for emulsifying or finely dispersing a fluorine-containing organic compound, the intended emulsion of dispersion can be obtained by conducting a customary emulsifying or dispersing operation in the presence of a compound of this invention represented by the above general formula (I). In this case, the compound of the general formula (I) is used in an amount of 0.001 to 3% by weight, preferably 0.005 to 1% by weight, practically 0.01 to 0.5% by weight. The stability of the resulting emulsion or dispersion can be highly improved by conducting the emulsifying or dispersing operation at an elevated temperture, preferably 50° to 150° C or performing the heat treatment, preferably at 50° to 150° C, after the emulsifying or dispersing operation.

It is permissible that a chemical reaction is allowed to advance during this emulsifying or dispersing operation, for instance, emulsion polymerization in the case of preparation of fluorine-containing resins.

Further, the fluorine-containing surface active agent of this invention can be used as an emulsifier for preparation of oxygen-transfusive agents for preservation of organs, blood transfusion of excessive hemorrhage patients and other purposes. In general, oxygen-transfusive agents are prepared by emulsifying or finely dispersing a liquid fluorine-containing organic compound having such a high oxygen-dissolving power that more than 30% by volume of oxygen can be dissolved therein in an atmosphere of purified oxygen, into an aqueous biological composition having a serumal function (for example, biological saline solution, sodium lactate-added biological saline solution, artificial serum, etc.) in the presence of an emulsifier according to a customary emulsifying or dispersing operation (for example, ultrasonic vibration treatment, high speed jetting treatment, etc.) so that the dispersed particles have a size smaller than 2 μ, preferably smaller than 0.25 μ. If a compound represented by the above general formula (I) is used as the emulsifier and the emulsifying or dispersing treatment is conducted at an elevated temperature or the heat treatment is carried out after the emulsifying or dispersing operation, an emulsion or fine dispersion having a much improved stability can be obtined. This emulsifying or dispersing operation may be performed at one stage, or it is possible to adopt a two-stage or multi-stage process in which a relatively concentrated emulsion or fine dispersion is first prepared and then the concentration is adjusted to a standard level at the second stage.

Still further, the fluorine-containing surface active agent of this invention can be used as an emulsifier for preparation of, for example, fluorine-containing resins by emulsion polymerization. The emulsion polymerization for preparation of fluorine-containing resins can be accomplished by emulsion-homopolymerizing a polymerizable fluorine-containing monomer such as ethylene tetrafluoride, ethylene trifluorochloride, propylene hexafluoride, vinylidene fluoride and vinyl fluoride or emulsion-copolymerizing a two-component or polycomponent copolymer system including at least two members of such polymerizable fluorine-containing monomers (e.g., a combination of ethylene tetrafluoride and propylene hexafluoride) or at least one member selected from such polymerizable fluorine-containing monomers and one or more of olefins such as ethylene, propylene, isobutylene and 1-butene in an aqueous medium in the presence of a known polymerization catalyst such as a peroxide catalyst and a redox type catalyst and an emulsifier under known reaction conditions, for examples, at a temperature of 0° to 150° C (preferably under heating) under a pressure of 0 to 100 atmospheres. The surface active agent of this invention can be used as the emulsifier for the above emulsion polymerization and can give good results. When the fluorine-containing surface active agent of this invention is used as the emulsifier for this emulsion polymerization, it is incorporated in an amount of, for example, 0.001 to 0.5% by weight, preferably 0.005 to 0.05% by weight.

In case of application of the compound of this invention to surface active agents or emulsifiers, the compounds of general formula (I-1), (I-2) and (I-3) can be used in the combination at any variable ratios and may be used in combination with the compounds having the following general formula (II-1) at the ratio from 1/9 to 9/1.

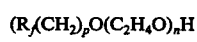  (II-1)

wherein R, *p* and *n* have the same meanings in general formula (I-1).

The above-mentioned oxygen-dissolving fluorine-containing organic compound includes hetero atom-containing or hetero atom-free perfluoro compounds and partially fluorinated organic compounds, and a chemically inactive perfluro compound in which all of the hydrogen atoms bonded to the carbon atoms in the molecule are substituted by fluorine atoms is especially preferred as an effective ingredient of an oxygen-transfusing agent. As examples of such preferred compounds there can be mentioned perfluoro tertiary amines having 8 to 15 carbon atoms such at tri-n-perfluorobutylamine, tri-n-perfluoropropylamine and perfluromethyl-perfluorocyclohexylamine; perfluoro alicyclic compounds having 6 to 15 carbon atoms such as perfluorodecaline, 1-perfluoromethyldecaline, perfluoroindane, perfluoromethylcyclohexane and 1,3,5-perfluorotrimethylcyclohexane, perfluoro aliphatic compounds such as perfluoro-n-nonane and perfluoro-n-decane; perfluoro ethers such as perfluoro-2,4-diethyltetrahydrofuran and perfluorodibenzyl ether; and polyfluorides of sulfur-containing compounds, e.g., perfluorodialkyl-S-tetrafluorides such as perfluorodipropyl-S-tetrafluoride and perfluorodibutyl-S-tetrafluoride, perfluoroalkyl-S-pentafluorides such as perfluorohexyl-S-pentafluoride and perfluorobutyl-S-pentafluoride, perfluoro(di)cycloalkyl-S-penta(tetra)-fluorides such as perfluorocyclohexyl-S-pentafluoride, and perfluorotetrahydrothinofuran tetrafluoride. It is preferred that such oxygen-dissolving fluorine-containing organic compound is used in an amount of 3 to 50% by weight based on the volume of the emulsion. If the compound is used in an amount smaller than 3%, the intended effect cannot be attained, and if the amount of the compound exceeds 50%, no particular improvement of properties of the resulting emulsion can be attained.

In this invention, other desired additives such as an emulsion stabilizer, for example, a polyhydric alcohol, e.g., glucose, a nutrient or pH adjusting agent when a blood substitute is prepared, an animal, vegetable oil or mineral oil when a lubricating oil is prepared, can be added at the time of the emulsifying operation, or they can be added after the emulsifying operation.

Emulsification can be accomplished by agitation or emulsifying under pressure or by using a homogenizer, and it is performed while the ingredients are being compounded or after completion of compounding of all the ingredients. One of the characteristic features of this invention is that when the specific surface active agent of this invention is employed, it is possible to obtain an emulsion which is finer and more stable than emulsions prepared by using hetero atom-substituted or unsubstituted perfluoro compounds.

Further, by the use of the surface active agent of this invention, it is made possible to provide a process for preparing an emulsion of a water-insoluble fluorine compound which can be used effectively as a blood substitute.

Still further, the surface active agent of this invention can be used as an emulsifier for preparation of a very stable emulsion of a water-insoluble fluorine compound which is effectively employed as a lubricating agent or additive of a cutting oil or the like. In this case, since the stability of the emulsion is very high and the perfluoro compound per se has a high stability, the emulsion can be used as a stable lubricating agent.

Still in addition, the fluorine-containing compound of this invention is effective as an active ingredient of a fire extinguishing composition of the aqueous flim type or a fire-extinguishing aqueous bubble composition, and this use will now be illustrated in more detail, though the use of the fluorine-containing surface active agent of this invention is not limited to this use alone. The fluorine-containing surface active agent of this invention is very effective as an active ingredient of a fire extinguishing composition of the aqueous film type or a fire-extinguishing aqueous bubble composition especially for liquid combustible substances having a high flammability such as gasoline, naphtha, ether and benzene and other liquid combustible substances containing such highly flammable substances. By virtue of the high activity, the fluorine-containing compound of this invention can cover promptly the surface of a petroleum type liquid fuel such as mentioned above in the form of an aqueous film having a long life, and hence, it can prevent evaporation or formation of a vapor of such liquid fuel for a long time. Further, even if such a film is broken by an external force, the aqueous film is restored very promptly. Therefore, an excellent fire extinguishing composition can be provided by using the fluorine-containing compound of this invention. Still further, such excellent fire-extinguishing effect can be attained even when hard water or water containing a polyvalent metal salt is employed.

Moreover, when the fluorine-containing compound of this invention is dissolved or dispersed in water or an organic solvent optionally together with other assistants and the resulting composition is sprayed or coated of fibrous products, natural leather products or artificial leather products, the touch and feel of the products can be improved and a prominent contamination-preventing effect can be imparted to these products.

Furthermore, the fluorine-containing surface active agent of this invention is effective and preferred as an emulsifier for fluorine-containing compounds inclusive of hetero atom-containing or hetero atom-free fluorocarbon compounds.

When the fluorine-containing surface active agent of this invention is used as the active ingredient of a fire-extinguishing composition, it is possible to form a fire-extinguishing composition composed essentially of the active ingredient alone, which is mixed and diluted with water when it is actually used (in this case, an aqueous solution formed by dilution with water is also included in the scope of this invention), but from the practical viewpoint, it is advantageous to form an aqueous fire-extinguishing composition comprising as indispensable components water and the fluorine-containing surface active agent of this invention.

Sufficient results can be obtained when the fluorine-containing surface active agent of this invention is incorporated into water at a relatively low concentration, but the amount incorporated of the surface active agent is so selected that an aqueous film can promptly be formed on the surface of a petroleum type liquid fuel or the like and scattering of the fuel vapor from the surface or catching fire thereof or re-combustion of the fuel can be effectively prevented. Practically, the concentration of the surface active agent is adjusted to 0.1 to 10% by weight for manufactured composition, and when the composition is actually used, it can be further diluted according to need so that the surface active agent concentration is 0.001 to 0.5% by weight. On actual application, the composition can be used as it is or preferably in the bubbled state. In the latter case, the composition can be bubbled by air, nitrogen gas, carbon dioxide gas, difluorordichloromethane vapor or other bubbling agent according to a known method.

The fire extinguishing composition, lubricant and other emulsions comprising the fluorine-containing surface active agent of this invention as the active ingredient can further comprise a fluorine-free surface active agent or other surface active agent within the object of this invention and if desired, the fire-extinguishing composition may further comprise a bubble stabilizer, a pour point depressant and/or other fire-extinguishing assistant. Still inaddition, on actual application, the fire extinguishing composition of this invention can be used in combination with other powdery fire extinguishing agents such as alkali bicarbonates, carbonic acid and alkali biphosphates. In case a fluorine-free surface active agent is used in combination with the fluorine-containing surface active agent of this invention, it is preferred that the fluorine-free surface active agent is incorporated in an amount of less than 25 parts per part of the surface active agent of this invention.

As the fluorine-free surface active agent to be preferably used in combination of the fluorine-containing surface active agent of this invention, there can be mentioned, for example, non-ionic surface active agents such as polyoxyethylene-polyoxypropylene glycol ethers of the following formula $$[HO(C_2H_4O)_a(C_3H_6O)_b(C_2H_4O)_cH] \qquad (A)$$

polyoxyethylene-polyoxybutylene glycol ethers of the following formula $$[HO(C_2H_4O)_a(C_4H_9O)_b(C_2H_4O)_cH] \qquad (B)$$

polyoxypropylene-polyoxyethylene glycol ethers of the following formula $$[HO(C_3H_6O)_a(C_2H_4O)_b(C_3H_6O)_cH] \qquad (C)$$

polyoxyethylene-polyoxypropylene alkyl ethers of the following formula $$[RO(C_3H_6O)_a(C_2H_4O)_bH] \qquad (D)$$

in which R is a lower or medium alkyl group, polyoxyethylene-polyoxypropylene alkaryl ethers of the following formula $$[R\cdot ArO(C_3H_6O)_a(C_2H_4O)_bH] \qquad (E)$$

in which R is a lower or medium alkyl group and Ar stands for an aromatic hydrocarbon residue such as a phenylene group,
polyoxyethylene-polyoxypropylene polyhydric alcohol ethers of the following formula $$R[O(C_3H_6O)_a(C_2H_4O)_bH]_n \qquad (F)$$

in which R is a lower or medium hydrocarbon residue having a valency of $n$, for example, $CH_2-CH-CH_2$ or $CH_3CH_2C(CH_2-)_3$, and $n$ is a number of 1 to 4,
polyoxyethylene-polyoxypropylene amine adducts of the following formula $$R[NR'(C_3H_6O)_a(C_2H_4O)_bH]_n \qquad (G)$$

in which R is a lower or medium hydrocarbon residue of a valency of $n$, for example, ethylene and propylene groups, R' is a lower alkyl group or a polyoxyalkylene chain represented by $(C_3H_6O)_a-(C_2H_4O)_bH$, and $n$ is a number of 1 to 2,
and polyoxyethylene-polyoxypropylene polyalkylene polyamine adducts, for example, $R_2NC_2H_4NRC_2H_4NR_2$ in which R is a polyoxyalkylene chain represented by $$(C_3H_6O)_a(C_2H_4O)_bH. \qquad (H)$$

In the foregoing formulae (A) to (H), $a$, $b$ and $c$ stand for the number of polymerization of the corresponding oxyalkylene group. Among the above exemplified compounds, those in which the molecular weight of the hydrophobic chain is 750 to 3000 and the molecular weight of the hydrophilic chain occupies 20 to 80% of the total molecular weight are especially preferred. In addition, there can be mentioned non-ionic surface active agents such as N,N-dihydroxyalkylamides (for example, higher fatty acid diethanol amides), polyoxyethylene medium or higher thioalcohol ethers (for example, $C_{12}H_{25}S(C_2H_4O)_{10}H$), alkylamine oxides (for example, N,N-dimethyl-laurylamine oxide), polyoxyethylene alkyl ethers of the formula $RO(C_2H_4O)_aH$ in which R is a medium or higher alkyl group, for example, an octyl or nonyl group, and $a$ is a number of 3 to 25, and polyoxyethylene alkaryl ethers of the formula $R\cdot ArO(C_2H_4O)_aH$ in which R is a medium or higher alkyl group, for example, an octyl or nonyl group, Ar stands for a divalent aromatic hydrocarbon residue, for example, a phenylene group, and $a$ is a number of 3 to 25.

As other surface active agents to be used conveniently in combination with the fluorine-containing surface active agent of this invention, there can be mentioned, for example, alkyl sulfonates such as sodium decanesulfonate, alkyl sulfates such as sodium laurylsulfate, alkyl phosphates such as sodium laurylphosphates, polyoxyethylene alkarylsulfates such as $C_8H_{17}C_6H_4O(C_2H_4O)_3C_2H_4OSO_3Na$, polyoxyethylene alkylarylphosphates such as $C_9H_{19}C_6H_4O(C_2H_4O)_4C_2H_4OPO_3K_2$, taurine derivatives such as $C_{11}H_{23}CON(CH_3)CH_2CH_2SO_3Na$, dialkylsulfosuccinates such as sodium dihexylsulfosuccinate, and the like.

As the bubble or form stabilizing agent to be optionally used in combination with the surface active agent of this invention, there can be mentioned known assistants, for example, protein type foaming agents, polyvinyl alcohol, high-molecular-weight polyoxyethylene oxides. As the pour point depressant and other assistant, there can be mentioned, for example, alkylene glycols such as ethylene glycol and propylene glycol, alkylene glycol ethers such as ethoxyethanol and butoxyethanol, low-molecular-weight polyalkylene glycols and their derivatives such as diethylene glycol, diethylene glycol butyl ether and dipropylene glycol, soluble alkali silicates such as sodium silicate in which the $SiO_2/Na_2O$ ratio is from 4 to 4.5, alkali phosphates, and the like.

The effect attained by a fire extinguishing composition comprising the fluorine-containing surface active agent of this invention is that when it is applied to extinguishing of fires of combustible liquids such as gasoline, naphtha and benzene and other solid combustible substances, the fires are promptly extinguished and re-combustion can be prevented for a long time by the aqueous film formed on the surfaces of the burning substances optionally together with bubbles, and even when muddy water, hard water or other foul water is employed, a higher fire-extinguishing effect can be attained than the fire-extinguishing effect attained by other fluorine type fire extinguishing compositions.

Another effect attained by this invention is that a novel fluorine-containing surface active agent giving a surface tension of about 20 dyn/cm or lower under practical conditions and having a very excellent emulsifying power can be provided. Still another effect attained by this invention is that a novel fluorine-containing surface active agent having a high surface activating property with a broad application range and a good compounding property comparable to those of ordinary hydrocarbon type surface active agents can be provided. Still in addition, according to one application embodiment of the surface active agent of this invention, a fluorine-containing organic compound can be effectively emulsified or finely dispersed and a very stable emulsion or fine dispersion of the fluorine-containing organic compond can be obtained.

Moreover, when the fluorine-containing surface active agent of this invention is used for formation of fluorine-containing resins by emulsion polymerization, preparation of oxygen-transfusive agents comprising an oxygen-dissolving fluorine-containing oganic compound, preparation of fine dispersions of a fluorine-containing organic compound that can be used for coating or lubricating, and for the like purposes, stable emulsions or fine dispersions having a much reduced particle size can be obtained.

The uses and effects of the fluorine-containing surface active agent of this invention are not limited to those mentioned above, and needless to say, it can be used as the main effective ingredient of fire-extinguishing liquids of the aqueous film type or the like.

The production of the fluorine-containing compound of this invention represented by the above general formula (I) will now be described more specifically by reference to the following Production Examples, but it must be noted that the scope of the invention is not limited by these Examples.

PRODUCTION EXAMPLE 1

A 100-ml capacity anti-corrosive pressure vessel was charged with 20 g (0.05 mole) of 1,1-dihydroperfluorooctanol [$CF_3(CF_2)_6CH_2OH$] and 0.2 g of KOH as a catalyst, and the mixture was cooled to 0°–5° C. Then, 47 g (0.881 mole) of propylene oxide was added to the mixture and the reaction vessel was sealed. The inside atmosphere was replaced by nitrogen, and the vessel was immersed in an oil bath and the reactants were heated at 100° C for 30 hours under agitation. The reaction pressure reached 11 kg/cm² at highest and was then lowered. Then, the reaction mixture was cooled to 0°–5° C and 12 g (0.3 mole) of ethylene oxide was added thereto, following which the vessel was sealed again and the inside atmosphere was replaced by nitrogen. Then, the reaction vessel was immersed in an oil bath again and the reaction mixture was heated at 100° C for 18 hours. The reaction pressure reached 8.5 kg/cm² at highest and was then lowered. After completion of the reaction, the reaction product liquid was taken out of the reaction vessel, and the catalyst was removed, followed by degasification. Thus was obtained 73 g of a reddish brown pasty substance, and as a result of the analysis the product was found to be $CF_3(CF_2)_6-CH_2O(C_3H_6O)_{14}(C_2H_4O)_5H$. The surface tension of an aqueous solution of the product was as follows:

0.1 w/v % : 15.9 dyn/cm 0.01 w/v % : 17.0 dyn/cm 0.001 w/v % : 41.5 dyn/cm

PRODUCTION EXAMPLE 2

A 300-ml capacity 4-neck separable flask equipped with an agitator, a dropping funnel and a thermometer was charged with 60 g (0.2 mole) of 1,1-dihydroperfluorohexanol [$CH_3(CF_2)_4CH_2OH$] and 5 g of $BF_3.O(C_2H_5)_2$ as a catalyst. The inside atmosphere was replaced by nitrogen and heating was started. When the temperature was elevated to 70° C, 116 g (2 moles) of propylene oxide was added dropwise from the dropping funnel. After completion of the dropwise addition, the mixture was heated at 70°–80° C for 2 hours under agitation. Then, 44 g (1 mole) of ethylene oxide was added dropwise from the dropping funnel and after completion of the dropwise addition, the mixture was heated at 70°–80° C for 2 hours under agitation. After completion of the reaction, the catalyst was removed, followed by degasification. Thus was obtained 201 g of a blackish brown pasty substance. As a result of the analysis, the product was found to be $CF_3(CF_2)_4CH_2O(C_3H_6O)_9(C_2H_4O)_4H$. The surface tension of an aqueous solution of the product was as follows:

0.1 w/v % : 16.0 dyn/cm 0.01 w/v % : 16.4 dyn/cm 0.001 w/v % : 42.0 dyn/cm

PRODUCTION EXAMPLE 3

A 1-l capacity autoclave was charged with 0.2 mole of 1,1-dihydroperfluoro-octanol, 1.6 mole of propylene oxide and 0.8 g of a 50 wt. % aqueous solution of caustic soda, and the inside atmosphere was substituted by nitrogen. The mixture was agitated at 120° C for 72 hours. The reaction pressure reached 8 kg/cm² at highest and was then lowered to the original pressure. The point at which the pressure was lowered to the original pressure was defined as the point of termination of the reaction (the same will apply hereinafter).

Then, 1.0 mole of ethylene oxide was added to the so obtained product, and after the inside atmosphere was replaced by nitrogen, the mixture was agitated at 120° C for 60 hours. The reaction pressure was elevated to 12 kg/cm² at highest and then lowered. The catalyst was removed from the so obtained product and the product was treated at 90° C under about 10 mm Hg for 2 hours for purification of the product. Thus was obtained 168 g of crude $C_7F_{15}CH_2O(C_3H_6O)_8(C_2H_4O)_5H$ in the form of a yellow viscous paste. The surface tension of an aqueous solution of this crude product was as follows:

0.1 % : 15.9 dyn/cm 0.01 % : 16.4 dyn/cm

PRODUCTION EXAMPLES 4 to 6

In the same manner as described in Production Example 3, the following fluorine-containing alcohols A, B and C as the starting substance were reacted with corresponding amounts of propylene oxide and ethylene oxide in two stages, and the resulting reaction mixtures were purified to obtain the following products A, B and C.

Starting Substances

A: 1,1,2,2-tetrahydroperfluoro-octyl alcohol
B: 1,1,2,2-tetrahydroperfluoro-octyl alcohol
C: 1,1,2,2-tetrahydroperfluorododecyl alcohol Reaction Products Production Example 4: $C_6F_{13}CH_2CH_2O(C_3H_6O)_7(C_2H_4O)_4H$
(product A, pasty)

Production Example 5: $C_6F_{13}CH_2CH_2O(C_3H_6O)_5(C_2H_4O)_{10}H$
(product B, pasty)

Production Example 6: $C_{10}F_{21}CH_2CH_2O(C_3H_6O)_7(C_2H_4O)_{12}H$
(product C, pasty)

The surface tension of a 0.1% aqueous solution of the product was as follows:
Product A: 15.8 dyn/cm
Product B: 17.0 dyn/cm
Product C: 19.2 dyn/cm

PRODUCTION EXAMPLE 7

0.1 Mole of a liquid adduct of ethylene oxide (1 mole) to 1,1,2,2-tetrahydroperfluoro-octyl alcohol was gradually added dropwise to 0.12 mole of fuming sulfuric acid (sulfur trioxide content of 60%) under cooling and agitation, and the mixture was reacted under agitation for 2 hours. The resulting brown reaction mixture was poured into ice pieces and diluted. The diluted mixture was neutralized with 18-N NaOH to obtain a crude product. Recrystallization gave light yellow sodium 1,1,2,2-tetrahydroperfluoro-octyl (oxyethylene) ether sulfate ($C_6F_{13}CH_2CH_2O-CH_2CH_2O-SO_3Na$). The surface tension of an aqueous solution of the product was as follows:

0.1 % : 20 dyn/cm 0.01 % : 28 cyn/cm

PRODUCTION EXAMPLE 8

0.15 Mole of sulfuric acid (100%) was gradually added dropwise to 0.1 mole of a liquid adduct of ethylene oxide (1 mole) to 1,1,2,2-tetrahydroperfluoro-octyl alcohol, which was being maintained at 30°–50° C. After completion of the dropwise addition, the reaction mixture was agitated for about 2 hours. The reaction mixture was diluted with ice pieces and anhydrous ethanol was added to the diluted mixture. Then, the mixture was neutralized with 18-N NaOH to remove the inorganic salt therefrom. The residual mixture was dried under reduced pressure to obtain sodium 1,1,2,2-tetrahydroperfluoro-octyl (oxyethylene) ether sulfate ($C_6F_{13}CH_2CH_2O-CH_2CH_2OSO_3Na$) in the form of a light yellow solid.

PRODUCTION EXAMPLE 9

0.1 Mole of a liquid adduct of propylene oxide (1 mole) to 1,1,2,2-tetrahydroperfluoro-octyl alcohol was gradually added dropwise under cooling and agitation to 0.12 mole of fuming sulfuric acid (sulfur trioxide content of 60%), and the mixture was reacted at 50°–70° C for 2 hours under agitation. After completion of the reaction, the resulting dark brown reaction mixture liquid was poured into ice pieces and diluted, and the diluted mixture was neutralized with 18-N NaOH to obtain a crude product. Recrystallization gave a purified product of sodium 1,1,2,2-tetraperfluoro-octyl (oxypropylene) ether sulfate ($C_6F_{13}CH_2CH_2O-C_3H_6O-SO_3Na$). The surface tension of an aqueous solution of the product was as follows:

0.1 % : 21 dyn/cm 0.01 % : 30 dyn/cm

PRODUCTION EXAMPLE 10

In dry benzene (containing pyridine as a hydrochloric acid acceptor), 0.1 mole of phosphorus oxychloride was gradually added to 0.1 mole of liquid 1,1,2,2-tetrahydroperfluoro-octyl-hepta (oxyethylene) ether at 0°–30° C in a nitrogen atmosphere. The mixture was hydrolyzed with water, neutralized with 18-N NaOH and treated with ethanol to remove the inorganic salt therefrom. The remaining mixture was dried to cause evaporation. Thus was obtained a crude product of sodium 1,1,2,2-tetrahydroperfluoro-octyl-hepta (oxyethylene) ether phosphate $[C_6F_{13}CH_2CH_2O-(CH_2CH_2O)_7-P(O)(ONa)_2]$ in the form of a paste.

PRODUCTION EXAMPLE 11

0.15 Mole of 100% sulfuric acid was gradually added dropwise to 0.1 mole of pasty crude 1,1,2,2-tetrahydroperfluoro-octyl-di (oxypropylene)-penta(oxyethylene) ether under agitation and cooling. Then, the mixture was further reacted for 2 hours. After completion of the reaction, the resulting brown reaction mixture was poured into ice pieces and diluted, and the diluted mixture was neutralized with 18-N NaOH and treated with ethanol to remove the inorganic salt. Thus was obtained a crude product of sodium 1,1,2,2-tetrahydroperfluoro-octyl-di (oxypropylene)-penta (oxyethylene) ether sulfate $[C_6F_{13}CH_2CH_2O(C_3H_6O)_2(CH_2CH_2O)_2(CH_2CH_2O)_5SO_3Na]$. The surface tension of an aqueous solution of the product was as follows:

0.1 % : 20 dyn/cm 0.01 % : 27 dyn/cm

PRODUCTION EXAMPLES 12 to 15

0.2 Mole of any of the following crude products of fluorine-containing alkyl-poly(oxyalkylene) ethers A, B, C and D was heated and to the resulting liquid was gradually added 0.06 mole of solid granular phosphorus pentoxide under violent agitation within a period of 15 minutes. Then, the mixture was heated at 100° C for more than 5 hours to complete the reaction.

After completion of the reaction, the reaction mixture was cooled, diluted with cold anhydrous ethanol, neutralized with an aqueous solution of sodium carbonate and dried.

The resulting mixture was treated with ethanol to remove the inorganic salt therefrom and 0.12–0.15 mole of the corresponding phosphate was obtained.

A: $C_7F_{15}CH_2O(C_3H_6O)_5(C_2H;hd 4O)_5H$
B: $C_6F_{13}CH_2CH_2O(C_2H_4O)_5H$
C: $C_6F_{13}CH_2CH_2O(C_2H_4O)_9H$
D: $C_{10}F_{21}CH_2CH_2O(C_2H_4O)_{10}H$

PRODUCTION EXAMPLES 16 and 17

0.05 Mole of phosphorus pentoxide was added under violent agitation to 0.1 mole of liquid 1,1,2,2-tetrahydroperfluoro-octyl (oxyethylene) ether being maintained at 30°-40° C, and the mixture was reacted at 70°-80° C for 2 hours. Water was added to the reaction mixture liquid, and the mixture was neutralized with 18-N NaOH and dried under evaporation to obtain a light yellow crude product of sodium 1,1,2,2-tetrahydrofluoro-octyl-(oxyethylene) either phosphate [$C_6F_{13}CH_2CH_2OC_2H_4OP(O)(ONa)_2$].

In the same manner as above, sodium 1,1,2,2-tetrahydroperfluoro-octyl-di (oxypropylene) ether phosphate was prepared from 1,1,2,2-tetrahydroperfluoro-octyl-di (oxypropylene) ether.

PRODUCTION EXAMPLE 18 and 19

0.05 Mole of phosphorus pentoxide was gradually added to 0.1 mole of liquid 1,1,2,2-tetrahydroperfluorododecylpenta (oxypropylene) ether [$C_{10}F_{21}CH_2CH_2O(C_3H_6O)_5H$] being maintained at 30°-60° C. Then, the mixture was reacted at 80°-ϕ° C for 2 hours under agitation. Water was added to the reaction mixture, and the mixture was neutralized with 18-N NaOH and dried under evaporation to obtain a light yellow pasty crude product of sodium 1,1,2,2-tetrahydroperfluorododecyl-penta (oxypropylene) ether phosphate [$C_{10}F_{21}CH_2CH_2O(C_3H_6O)_5P(O)(ONa)_2$].

In the same manner as above, powdery sodium 1,1,2,2-tetrahydroperfluorododecyl (oxyethylene) ether phosphate [$C_{10}F_{21}CH_2CH_2O(C_2H_4O)PO_3Na_2$] was prepared from 1,1,2,2-tetrahydroperfluorododecyl (oxyethylene) ether.

PRODUCTION EXAMPLE 20

0.05 Mole of phosphorus pentoxide was added under agitation at 30°-40° C to 0.1 mole of oily 1,1,2,2-tetrahydroperfluoro-octyl-octa (oxypropylene)-pentadeca-(oxyethylene) ether, and the mixture was reacted under agitation at 70°-80° C. The reaction mixture was hydrolyzed with water, and the mixture was neutralized with 18-N NaOH and dried under evaporation to obtain light yellow sodium 1,1,2,2-tetrahydroperfluoro-octyl-octa (oxypropylene)-penta (oxyethylene) ether phosphate [$C_6F_{13}CH_2CH_2O(C_3H_6O)_8(CH_2CH_2O)_5P(O)(ONa)_2$].

PRODUCTION EXAMPLE 21

0.05 mole of phosphorus pentoxide was gradually added under agitation to 0.1 mole of liquid 1,1,2,2-tetrahydroperfluorododecyl-hepta (oxypropylene)-pentadeca (oxyethylene) ether, and the mixture was reacted under agitation at 80°-100° C for 2 hours. Water was added to the reaction mixture, and the mixture was neutralized with 18-N NaOH and dried under evaporation to obtain a light yellow pasty crude product of sodium 1,1,2,2-tetrahydroperfluorododecyl-hepta (oxypropylene)-pentadeca (oxyethylene) ether phosphate [$C_{10}F_{21}CH_2CH_2O(C_3H_6O)_7(CH_2CH_2O)_{15}P(O)(ONa)_2$]. The surface tension of an aqueous solution of the product was as follows:

0.1 % : 23 dyn/cm 0.01 % : 30 dyn/cm

PRODUCTION EXAMPLES 22 to 26

A flask equipped with a reflux cooler, an agitator and a thermometer was charged with 0.1 mole of tolylene diisocyanate, and 0.1 mole of the following fluorine-containing alkyl-poly (oxyalkylene) ether A, B, C or D as starting compounds was added thereto. The mixture was agitated at 90°-100° C for 4 hours. Then, 0.1 mole of polyethylene glycol having a molecular weight of about 500 was added to the resulting reaction mixture, and agitation was continued for 1 hour at 100°-110° C.

After the reaction, the presence of the free isocyanate group was not detected at all.

The so obtained reaction mixture was treated at 90° C under about 10 mm Hg for 2 hours. In this manner, the following products A, B, C and D were obtaind.

Starting compound A: 1,1-dihydroperfluoro-octyl-di (Oxypropylene) ether

Starting compound B: 1,1,2,2-tetrahydroperfluoro-octyl-penta (oxyethylene) ether Starting compound C: 1,1,2,2-tetrahydroperfluoro-octyl-penta (oxypropylene) ether Starting compound D: 1,1,2,2-tetrahydroperfluorododecyl-penta (oxypropylene) ether Product A: $C_7F_{15}CH_2O(C_3H_6O)_2CONHC_6H_3(CH_3)NHCO(OC_2H_4)_{12}OH$ Product B: $C_6F_{13}CH_3CH_2O(C_2H_4O)_5CONHC_6H_3(CH_3)-NHCO(OC_2H_4)_{12}OH$ Product C: $C_6F_{13}CH_2CH_2O(C_3H_6O)_5CONHC_6H_3)CH_3)NHCO-(OC_2H_4)_{12}OH$ Product D: $C_{10}F_{21}CH_2CH_2O(C_{3,l}H_6O)_5CONHC_6H_3(CH_3)-NHCO(OC_2H_4)_{12}OH$ In the same manner as described above, the following product E was prepared from the above starting compound C, tolylene diisocyanate and polyoxyethylene glycol having a molecular weight of about 1000.

Product E: $C_6F_{13}CH_2CH_2O(C_3H_6O)_5CONHC_6H_3(CH_3)-NACO(OC_2H_4)_{25}OH$

Some Examples of compositions containing the surface active agent of this invention will now be illustrated, but it must be noted that the scope of the invention is not limited by these Examples.

COMPOSITION EXAMPLE 1

Component I: $C_7F_{15}CH_2O(C_3H_6O)_m(C_3H_4O)_nH$, 90—60 wt. %

Component II: $C_7F_{15}CH_2O(C_2H_4O)_pH$, 10—40 wt. %

Notes:
1. $m$ is 6.8 on the average
2. $n$ is 3.9 on the average
3. $p$ is 4.9 on the average A 0.01-0.1% aqueous solution of the product had a surface tension of 17-21 dyn/cm.

COMPOSITION EXAMPLE 2

Component I: $C_6F_{13}CH_2CH_2O(C_3H_4O)_nH$, 90-50 wt. %

Component II: $C_6F_{13}CH_2CH_2O(C_2H_4O)_pH$, 10-50 wt. %

Notes:
1. $m$ is 7.8 on the average
2. $n$ is 4.1 on the average
3. $p$ is 6.3 on the average A 0.01-0.1% aqueous solution of the product had a surface tension of 17-20 dyn/cm.

COMPOSITION EXAMPLE 3

Component I: $C_lF_{2l+1}CH_2CH_2O(C_3H_6O)_m(C_2H_4O)_nH$, 90-50 wt. %

Component II: $C_lF_{2l+1}CH_2CH_2O(C_2H_4O)_pH$, 10-50 wt. %

Notes:
1. $l$ is 7.5 on the average
2. $m$ is 9.5 on the average

3. $n$ is 5.2 on the average
4. $p$ is 4.3 on the average

A 0.01–0.1% aqueous solution of the product had a surface tension of 19–20 dyn/cm.

COMPOSITION EXAMPLE 4

Component I: $C_6F_{13}C_2H_4O(C_2H_4O)_nPO_3Na_2$, 15–35 wt.%

Component II: $C_6F_{13}C_2H_4O(C_2H_4O)_nH$, 85–65 wt.%

Note:
$n$ is 3.1 on the average

A 0.01–0.1% aqueous solution of the product had a surface tension of 17–23 dyn/cm.

COMPOSITION EXAMPLE 5

Component I: $C_lF_{2l+1}C_2H_4O(C_2H_4O)_nPO_3Na_2$, 15–35 wt.%

Component II: $C_lF_{2l+1}C_2H_4O(C_2H_4O)_nH$, 85–65 wt.%

Notes:
1. $l$ is 8.5 on the average
2. $n$ is 4.3 on the average

A 0.01–0.1% aqueous solution of the product had a surface tension of 17–19 dyn/cm.

COMPOSITION EXAMPLE 6

Component I: $C_7F_{15}CH_2O(C_3H_6O)_m(C_2H_4O)_nPO_3Na_2$, 50–20 wt.%

Component II: $C_7F_{15}CH_2O(C_3H_6O)_m(C_2H_4O)_nH$, 50–80 wt.%

Notes:
1. $m$ is a 4.8 on the average
2. $n$ is 3.6 on the average

A 0.01–0.1% aqueous solution of the product had a surface tension of 18–26 dyn/cm.

COMPOSITION EXAMPLE 7

Component I: $C_6F_{13}C_2H_4O(C_3H_6O)_m(C_2H_4O)_nPO_3Na_2$, 50–20 wt.%

Component II: $C_6F_{13}C_2H_4O(C_3H_6O)_m(C_2H_4O)_nH$, 50–80 wt.%

Notes:
1. $m$ is 7.8 on the average
2. $n$ is 4.1 on the average

A 0.1% aqueous solution of the product had a surface tension of 17 to 21 dyn/cm.

COMPOSITION EXAMPLE 8

Component I: $C_lF_{2l+1}C_2H_4O(C_3H_6O)_m(C_2H_4O)_nPO_3Na_2$, 50–20 wt.%

Component II: $C_lF_{2l+1}C_2H_4O(C_3H_6O)_m(C_2H_4O)_nH$, 50–80 wt.%

Notes:
1. $l$ is 7.5 on the average
2. $m$ is 5.8 on the average
3. $n$ is 3.5 on the average A 0.01–0.1% aqueous solution of the product had a surface tension of 19–21 dyn/cm.

COMPOSITION EXAMPLE 9

Component I: $C_7F_{15}CH_2O(C_3H_6O)_m(C_2H_4C)_nSO_3Na$, 20–60 wt.%

Component II: $C_7F_{15}CH_2O(C_3H_6O)_m(C_2H_4O)_nH$, 80–40 wt.%

Notes:
1. $m$ is 6.8 on the average
2. $n$ is 3.9 on the average

COMPOSITION EXAMPLE 10

Component I: $C_6F_{13}C_2H_4O(C_3H_6O)_m(C_2H_4O)_nSO_3Na$, 20–60 wt.%

Component II: $C_6F_{13}C_2H_4O(C_3H_6O)_m(C_2H_4O)_nH$, 80–40 wt.%

Notes:
1. $m$ is 7.8 on the average
2. $n$ is 4.1 on the average

COMPOSITION EXAMPLE 11

Component I: $C_lF_{2l+1}C_2H_4O(C_3H_6O)_m(C_2H_4O)_nSO_3Na$, 20–60 wt.%

Component II: $C_lF_{2l+1}C_2H_4O(C_3H_6O)_m(C_2H_4O)_nH$, 80–40 wt.%

Notes:
1. $l$ is 7.5 on the average
2. $m$ is 5.8 on the average 3. $n$ is 3.5 on the average

COMPOSITION EXAMPLE 12

Component I: $C_6F_{13}C_2H_4O(C_2B_4O)_pSO_3Na$, 10–25 wt.%

Component II: $C_6F_{13}C_2H_4O(C_2H_4O)_qH$, 90–75 wt.%

Notes:
1. $p$ is 6.5 on the average
2. $q$ is 4.9 on the average

A 0.001–0.1% aqueous solution of the product had a surface tension of 15–43 dyn/cm.

COMPOSITION EXAMPLE 13

Component I: $C_lF_{2l+1}C_2H_4O(C_2H_4O)_nSO_3Na$, 15–25 wt.%

Component II: $C_lF_{2l+1}C_2H_4O(C_2H_4O)_nH$, 85–75 wt.%

Notes:
1. $l$ is 8.5 on the average
2. $n$ is 3.8 on the average

A 0.001–0.1% aqueous solution of the product had a surface tension of 16–42 dyn/cm.

COMPOSITION EXAMPLE 14

Component I: $C_7F_{15}CH_2O(C_2H_4O)_nSO_3Na$, 10–25 wt.%

Component II: $C_pF_{2p+1}C_2H_4O(C_2H_4O)_qH$, 90–75 wt.%

Notes:
1. $n$ is 6.0 on the average
2. $p$ is 8.5 on the average 3. $q$ is 3.1 on the average A 0.001–0.1% aqueous solution of the product had a surface tension of 17–40 dyn/cm.

COMPOSITION EXAMPLE 15

Component I: $C_6F_{13}C_2H_4O(C_2H_4O)_3CONHC_6H_3(CH_3)NHCOO—(C_2H_4O)_{14}H$, 80–20 wt.%

Component II: $C_6F_{13}C_2H_4O(C_2H_4O)_3H$, 20–80 wt.%

A 0.1% aqueous solution of the product had a surface tension of 14–20 dyn/cm.

COMPOSITION EXAMPLE 16

Component I: $C_lF_{2l+1}C_2H_4O(C_2H_4O)_4CONHC_6H_3(CH_3)NHCOO—(C_2H_4O)_{14}H$, 80–20 wt.%

Component II: $C_lF_{2l+1}C_2H_4O(C_2H_4O)_4H$, 20–80 wt.%

Note:
1. $l$ is 8.5 on the average

A 0.1% aqueous solution of the product had a surface tension of 18-20 dyn/cm.

COMPOSITION EXAMPLE 17

Component I: $C_7F_{15}CH_2O(C_2H_4O)_5CONHC_6H_3(CH_3)NHCOO-(C_2H_4O)_{14}H$, 80-20 wt.%

Component II: $C_7F_{15}CH_2O(C_2H_4O)_5H$, 20-80 wt.%

A 0.1% aqueous solution of the product had a surface tension of 15-21 dyn/cm.

Examples of the application of the surface active agent of this invention to emulsifier will now be described, but it must be noted that the scope of the invention is not limited by these Examples.

EMULSIFIER EXAMPLES 1 to 8 AND COMPARATIVE EXAMPLE 1

The stabilities of emulsion of water, 20 vol.% of perfluoromethyldecalin and 0.4 wt.% of crude surface active agent A, B, C, D, E, F, G and H having the following formula and emulsified with homomixer (10 minutes) and super sonic wave (10 KHz, 10 minutes) as usual, were examined in a thin glass tubes.

For comparison, the stability was examined similarly in case of the salt of perfluorooctanoic acid.

Good emulsion was obtained in case of both surface active agent A-H and the comparative surface active agent, but after 3 days, the tendency toward sedimentation and concentration of dispersed granulars of comparative emulsion were observed, and after 5 days, the layer of perfluoromethyldecalin was observed in comparative emulsion, while no change, no sedimentation and no separation were observed in the emulsions used the surface active agent A-H.

Surface active agent;
A: $C_6F_{13}C_2H_4O(C_3H_6O)_5(C_2H_4O)_{15}H$
B: $C_6F_{13}C_2H_4O(C_2H_4O)_{10}PO_3Na_2$
C: $C_6F_{13}C_2H_4O(C_3H_6O)_2SO_3Na$
D: $C_{10}F_{21}C_2H_4O(C_2H_4O(C_2H_4O)_5CONHC_6H_3(CH_3)NHCOO(C_2H_4O)_{12}H$
E: $C_{10}F_{21}C_2H_4OC_3H_6O(C_2H_4O)_{10}H$
F: $C_{10}F_{21}C_2H_4O(C_3H_6O)_5(C_2H_4O)_5PO_3Na_2$
G: $C_{10}F_{21}C_2H_4O(C_2H_4O)_5SO_3Na$
H: $C_6F_{13}C_2H_4O(C_3H_6O)_5CONHC_6H_3(CH_3)NHCOO(C_2H_4O)_{25}H$

EMULSIFIER EXAMPLES 9 AND 10 AND COMPARATIVE EXAMPLE 2

The stabilities of emulsions of the same composition as Examples of application to emulsifier 1 and 2 and Comparative Example of application to emulsifier 1 were examined, but, in this case, the emulsions were heated at 90° C for 30 minutes.

No change was observed in the case of Examples of application to emulsifier 1 and 2 but the sedimentations of dispersed granular and the layer of perfluoromethyldekalin were observed after 4 days.

Examples of fire-extinguishing compositions containing as the active ingredient the fluorine-containing surface active agent of this invention will now be described, but it must be noted that the scope of the invention is not limited by these Examples.

FIRE-EXTINGUISHING COMPOSITION EXAMPLES 1 TO 4

By employing the following fluorine-containing compounds A, B, C or D, fire-extinguishing compositions having the following components were prepared. When these compositions were subjected to the bubbling test described below, in each composition catching fire was not caused to occur.

RECIPE OF FIRE-EXTINGUISHING COMPOSITION

Fluorine-containing surface active agent of this invention: 0.1-0.2 wt.%
Commercially available fluorine-free surface active agent*: 0.0 or 0.1 wt.%
Polyethylene oxide of molecular weight of 80,000: 0.5-1 wt.%
Dipropylene glycol: 0.5-1 wt.%
Diethylene glycol: 0.5-1 wt.%
Diethylene glycol butyl ether: 1-2 wt.%
Acetic acid: 0.01-0.02 wt.%
Water: balance

*: Pluronic L64 (manufactured by Asahi Denka Kogyo K.K.) Bubbling Test:

The aqueous composition to be tested was bubbled with air and applied to the surface of gasoline placed in a Petri dish. Then, ignition was tried with use of flames.

Fluorine-Containing Surface Active Agents

A: $C_6F_{13}CH_2CH_2O(C_3H_6O)_{10}(C_2H_4O)_3H$
B: $C_6F_{13}CH_2CH_2O(C_3H_6O)_{10}(C_2H_4O)_3PO_3Na_2$
C: $C_{10}F_{21}CH_2CH_2O(C_2H_4O)_2SO_3Na$
D: $C_7F_{15}CH_2O(C_3H_6O)_2CONHC_6H_3(CH_3)NHCOO(C_2H_4O)_{12}H$

Other uses of the fluorine-containing surface active agent of this invention will now be illustrated by reference to the following Application Examples that by no means limit the scope of this invention.

APPLICATION EXAMPLE 1 and 2

The following crude compound A or B was incorporated in an amount of 0.1-0.5% into a sodium hypochlorite solution of the following composition to obtain a homogeneous bleaching detergent composition. In the case of each of the compounds A and B, the resulting composition had a good storage stability and exhibited high bleaching, sterilizing and detergent effects at an ordinary application concentration. In view of the fact that known conventional surface active agents were not dissolved in the above solution to such an extent that their surface activating properties would be fully utilized or they were decomposed in a relatively short time, it was seen that the fluorine-containing surface active agents of this invention had very excellent properties.

Sodium Hypochlorite Solution

NaClO: 6.5%
NaCl: 5.4%
NaSiO$_3$: 0.5%
Water: balance

Fluorine-Containing Surface Active Agents

A: $C_7F_{15}CH_2O(C_2H_4O)_{15}PO_3Na_2$
B: $C_6F_{13}CH_2CH_2O(C_3H_6O)_5(C_2H_4O)_{15}SO_3Na$

APPLICATION EXAMPLE 3 TO 6

By employing the following crude compounds A to D, the cutting test was conducted under the following conditions.

Processing Conditions:

Machine used: lathe

Tool used: SKH 4A form (0, 20, 6, 6, 8, 0, 0)
Material cut: S45C

Cutting Conditions

Cutting speed: 40 m/min
Feed rate: 0.2 m/rev
Cut depth: 1 cm
Flow rate of cutting oil: 1 l/min (40 times dilution)

Emulsions prepared by using the compounds A to D of this invention exhibited good working properties and high working efficiencies and could gave smooth processed surfaces to cut products. Thus, it was confirmed that these compounds of this invention were very excellent as agents for cutting oils.

Compounds:

A: $C_6F_{13}CH_2CH_2O(C_3H_6O)_{15}(C_2H_4O)_2H$
B: $C_6F_{13}CH_2CH_2O(C_3H_6O)_{15}PO_3Na_2$
C: $C_{10}F_{21}CH_2CH_2O(C_3H_6O)_{10}SO_3Na$
D: $C_6F_{13}CH_2CH_2O(C_3H_6O)_{10}CONHC_6H_3(CH_3)NHCO(OC_2H_4)_5OH$

What is claimed is:

1. A compound having the formula $$R_f(CH_2)_pO(RO)_mCONHR'NHCOO(C_2H_4O)_nH$$

wherein $R_f$ is perfluoroalkyl having 4 to 14 carbon atoms, $p$ is a number of from one to 10 and $R_f(CH_2)_p$- has from 6 to 16 carbon atoms; R is alkylene having from 2 to 4 carbon atoms; R' is alkylene, arylene or alkarylene having from 2 to 8 carbon atoms; $m$ is a number of from one to 50; and $n$ is a number of from one to 50.

2. A compound as claimed in claim 1, wherein $m$ is a number from one to 25; $n$ is a number of from one to 25; and $p$ is a number of from one to 2.

3. A compound as claimed in claim 1 in which R is ethylene or propylene.

4. A compound as claimed in claim 3 in which $m$ is from one to 15; $n$ is from 10 to 25; and $p$ is from one to 2.

5. A compound as claimed in claim 1 having the formula

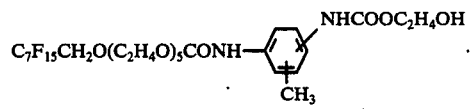

6. A compound as claimed in claim 1 having the formula

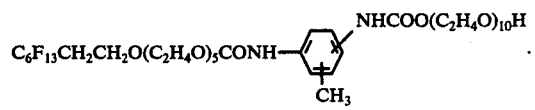

7. A compound as claimed in claim 1 having the formula

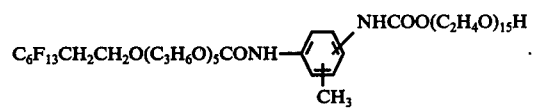

8. A compound as claimed in claim 1 having the formula

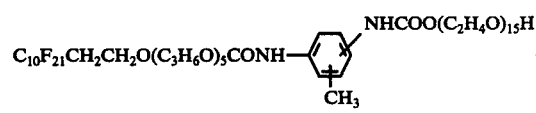

9. A compound as claimed in claim 1 having the formula

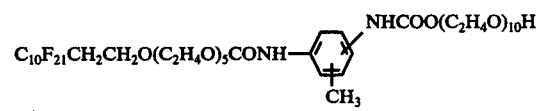

10. A compound as claimed in claim 4 in which R' is

* * * * *